US010842658B2

(12) United States Patent
Rincon

(10) Patent No.: US 10,842,658 B2
(45) Date of Patent: *Nov. 24, 2020

(54) ENDOPROTHESIS DELIVERY SYSTEM

(71) Applicant: Cardinal Health Switzerland 515 Gmbh, Bar Zug (CH)

(72) Inventor: Cesar Alberto Rincon, Union City, CA (US)

(73) Assignee: Cardinal Health Switzerland 515 GmbH, Bar Zug (CH)

( * ) Notice: Subject to any disclaimer, the term of this patent is extended or adjusted under 35 U.S.C. 154(b) by 206 days.

This patent is subject to a terminal disclaimer.

(21) Appl. No.: 15/973,207

(22) Filed: May 7, 2018

(65) Prior Publication Data

US 2018/0250149 A1    Sep. 6, 2018

Related U.S. Application Data

(63) Continuation of application No. 14/313,493, filed on Jun. 24, 2014, now Pat. No. 9,987,156, which is a
(Continued)

(51) Int. Cl.
*A61F 2/95* (2013.01)
*A61F 2/962* (2013.01)
(Continued)

(52) U.S. Cl.
CPC ............... *A61F 2/962* (2013.01); *A61F 2/07* (2013.01); *A61F 2/95* (2013.01); *A61F 2/954* (2013.01);
(Continued)

(58) Field of Classification Search
CPC .. A61F 2/95; A61F 2/954; A61F 2/962; A61F 2/966; A61F 2002/9505;
(Continued)

(56) References Cited

U.S. PATENT DOCUMENTS 5,201,757 A    4/1993   Heyn et al.
5,480,423 A    1/1996   Ravenscroft et al.
(Continued)

FOREIGN PATENT DOCUMENTS

DE    102006053748    4/2008
EP         1440673    7/2004
(Continued)

OTHER PUBLICATIONS

European Search Report dated Aug. 31, 2010 for corresponding Patent Appln. No. 10166254.2.
(Continued)

*Primary Examiner* — Melanie R Tyson
(74) *Attorney, Agent, or Firm* — Dergosits & Noah LLP; Todd A. Noah

(57) ABSTRACT

An endoprosthesis delivery system includes a wire holder on a distal section of an elongated shaft with a plurality of wires extending distally from the wire holder and, in a secured position, terminating in a distal receiver attached to the elongated shaft distal to the wire holder. A single wire attached to the wire holder and extending proximally along the delivery system to a point easily accessible by the operator may be pulled proximally to move the wires out of the distal receiver and release the endoprosthesis.

10 Claims, 15 Drawing Sheets

Related U.S. Application Data continuation of application No. 12/489,738, filed on Jun. 23, 2009, now Pat. No. 8,771,333.

(51) Int. Cl.
| | | |
|---|---|---|
| *A61F 2/07* | (2013.01) | |
| *A61F 2/954* | (2013.01) | |
| *A61F 2/06* | (2013.01) | |
| *A61F 2/89* | (2013.01) | |

(52) U.S. Cl.
CPC .............. *A61F 2/89* (2013.01); *A61F 2/9517* (2020.05); *A61F 2/9522* (2020.05); *A61F 2002/065* (2013.01); *A61F 2002/075* (2013.01); *A61F 2002/9505* (2013.01); *A61F 2002/9511* (2013.01); *A61F 2220/0075* (2013.01); *A61F 2250/0036* (2013.01)

(58) Field of Classification Search
CPC ...... A61F 2002/9511; A61F 2002/9517; A61F 2002/9534; A61F 2002/9665
See application file for complete search history.

(56) References Cited

U.S. PATENT DOCUMENTS

| | | | |
|---|---|---|---|
| 5,562,726 A | 10/1996 | Chuter | |
| 5,776,142 A | 7/1998 | Gunderson | |
| 5,824,041 A | 10/1998 | Lenker et al. | |
| 5,824,058 A | 10/1998 | Ravenscroft | |
| 5,968,052 A | 10/1999 | Sullivan, III et al. | |
| 6,077,296 A | 6/2000 | Shokoohi et al. | |
| 6,254,609 B1 | 7/2001 | Vrba et al. | |
| 6,344,044 B1 | 2/2002 | Fulkerson et al. | |
| 6,565,597 B1 | 5/2003 | Fearnot et al. | |
| 6,872,224 B1 | 3/2005 | Moretra et al. | |
| 7,101,390 B2 | 9/2006 | Nelson | |
| 7,147,657 B2 | 12/2006 | Chiang | |
| 7,264,632 B2 | 9/2007 | Wright | |
| 7,297,156 B2 | 11/2007 | Nelson | |
| 7,335,224 B2 | 2/2008 | Ohlenschlaeger | |
| 7,611,528 B2 | 11/2009 | Goodson, IV | |
| 7,632,298 B2 | 12/2009 | Hijlkema et al. | |
| 7,637,932 B2 | 12/2009 | Bolduc et al. | |
| 7,763,063 B2 | 7/2010 | Arbefeuille et al. | |
| 7,815,671 B2 | 10/2010 | Wright et al. | |
| 7,823,267 B2 | 11/2010 | Bolduc | |
| 7,909,863 B2 | 3/2011 | Hartley et al. | |
| 7,942,924 B1 | 5/2011 | Perez et al. | |
| 7,959,661 B2 | 6/2011 | Hijlkema et al. | |
| 8,043,354 B2 | 10/2011 | Greenberg et al. | |
| 8,062,345 B2 | 11/2011 | Ouellette et al. | |
| 8,092,519 B2 | 1/2012 | Bolduc | |
| 8,109,986 B2 | 2/2012 | Styrc | |
| 8,449,595 B2 | 5/2013 | Ouellette et al. | |
| 8,500,792 B2 | 8/2013 | Berra | |
| 8,690,897 B2 | 4/2014 | Bolduc | |
| 8,876,877 B2 | 11/2014 | Argentine | |
| 9,173,755 B2 | 11/2015 | Berra et al. | |
| 9,220,617 B2 | 12/2015 | Berra | |
| 9,987,156 B2 * | 6/2018 | Rincon | .................... A61F 2/07 |
| 2001/0049547 A1 | 12/2001 | Moore | |
| 2002/0099432 A1 | 7/2002 | Yee | |
| 2004/0093063 A1 | 5/2004 | Wright et al. | |
| 2004/0138734 A1 | 7/2004 | Chobotov et al. | |
| 2004/0148008 A1 | 7/2004 | Goodson, IV et al. | |
| 2004/0243215 A1 | 12/2004 | Nelson | |
| 2005/0049674 A1 | 3/2005 | Berra et al. | |
| 2005/0090834 A1 | 4/2005 | Chiang et al. | |
| 2005/0107862 A1 | 5/2005 | Ohlenschlaeger | |
| 2005/0131514 A1 | 6/2005 | Hijlkema et al. | |
| 2006/0004433 A1 | 1/2006 | Greenberg et al. | |
| 2006/0188408 A1 | 8/2006 | Berra et al. | |
| 2008/0027529 A1 | 1/2008 | Hartley et al. | |
| 2008/0071343 A1 | 3/2008 | Mayberry | |
| 2008/0077227 A1 | 3/2008 | Ouellette et al. | |
| 2008/0234797 A1 | 9/2008 | Styrc | |
| 2008/0264102 A1 | 10/2008 | Berra | |
| 2009/0030497 A1 | 1/2009 | Metcalf et al. | |
| 2009/0099637 A1 | 4/2009 | Barthold et al. | |
| 2009/0264992 A1 | 10/2009 | Fleming, III | |
| 2009/0270967 A1 | 10/2009 | Fleming, III et al. | |
| 2009/0287299 A1 | 11/2009 | Tabor et al. | |
| 2010/0010617 A1 | 1/2010 | Goodson, IV et al. | |
| 2010/0185230 A1 | 7/2010 | Horan et al. | |
| 2010/0274187 A1 | 10/2010 | Argentine | |
| 2010/0292778 A1 | 11/2010 | Roeder et al. | |
| 2012/0010696 A1 | 1/2012 | Greenberg et al. | |

FOREIGN PATENT DOCUMENTS

| | | |
|---|---|---|
| WO | 00/65270 | 11/2000 |
| WO | 08/98255 | 8/2008 |

OTHER PUBLICATIONS

Australian Office Action, dated Jun. 20, 2014, for related Australian Patent Appln. No. 2010202531.

Australian Office Action, dated May 9, 2016, for related Australian Patent Appln. No. 2015203704.

* cited by examiner

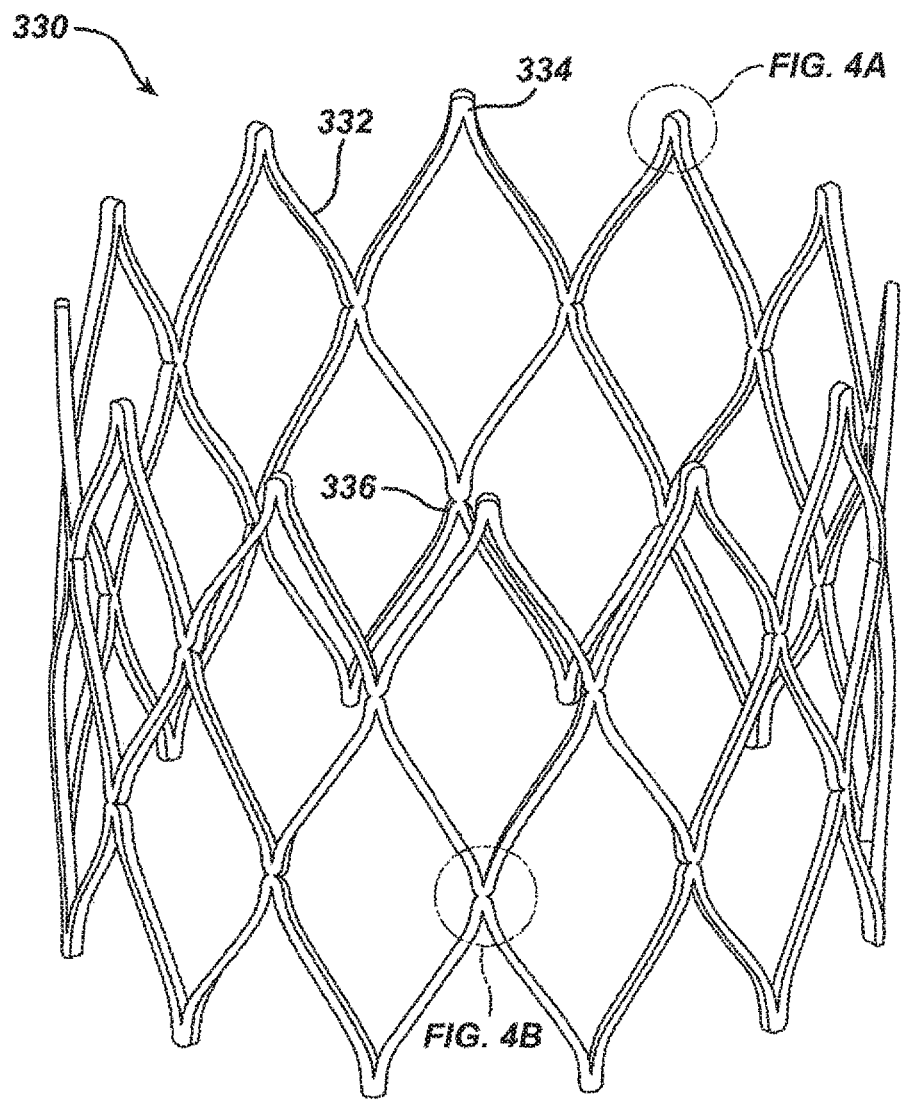

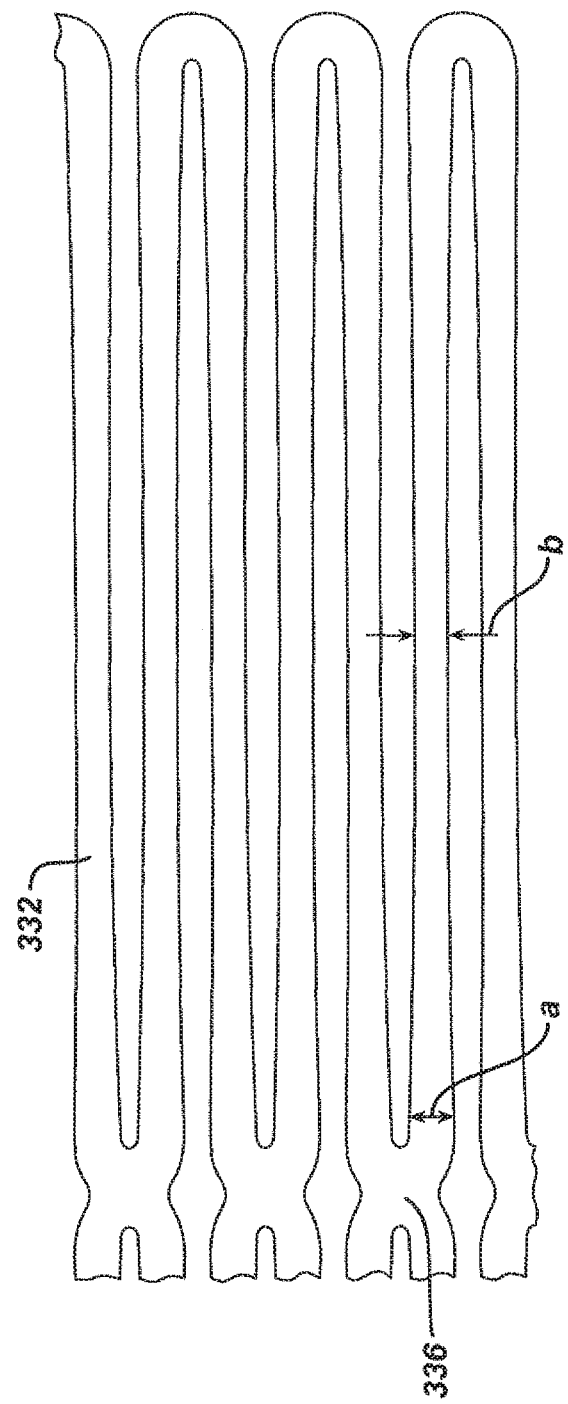

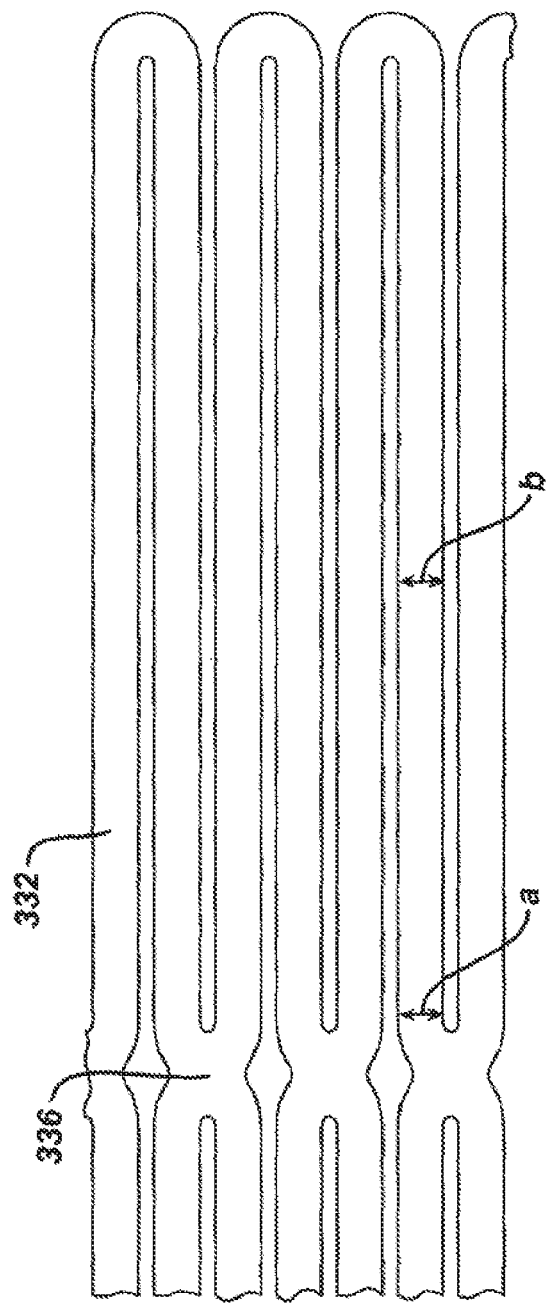

ENDOPROTHESIS DELIVERY SYSTEM

PRIORITY CLAIM

This application is a continuation of U.S. application Ser. No. 14/313,493, filed on Jun. 24, 2014, which is a continuation of U.S. application Ser. No. 12/489,738, filed on Jun. 23, 2009, now U.S. Pat. No. 8,771,333.

FIELD OF THE PRESENT DISCLOSURE

The present invention relates to aneurismal repair devices, and more particularly, to devices for restraining the cranial end of an endoprosthesis of an aneurismal repair device until the remaining portion of the endoprosthesis is deployed and fully expanded and then deploying the cranial end.

DISCUSSION OF RELATED ART

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via a transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3 F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta. In addition, the endoprostheses should preferably be percutaneously delivered and deployed such that surgical cut down is unnecessary.

During deployment of a typical device, the endoprosthesis is held stationary while an outer catheter sheath is retracted and the endoprosthesis expands into position due to the self-expanding properties of the underlying stent structure. Due to the potential tortuous nature of the human anatomy, the delivery catheter containing the endoprosthesis generally lies up against one side of the vessel prior to deployment. It has been observed in testing that when a supra renal stent with barbs is the first portion of the endoprosthesis to expand, the barbs closest to the vessel wall may make premature contact with the wall before the stent has had a chance to fully expand. This creates a situation where the portion of the stent farthest away from the wall during expansion actually accounts for a disproportionate amount of the expansion of the stent in order for the entire stent to meet the internal diameter of the vessel. The sections of the stent that are up against the wall do not fully expand and the stent will not achieve full opposition against the vessel wall. Accordingly, it would be highly advantageous to have a device that delays the opening of the cranial end until the remaining portions are deployed.

SUMMARY

The present invention overcomes the disadvantages associated with currently utilized aneurismal repair devices and their associated deployment mechanisms.

In accordance with a first aspect, the present invention is directed to a stent-graft securement device for a catheter based stent-graft delivery system. The stent-graft securement device comprising a holding device which is integral with the catheter based stent-graft delivery system, the holding device including a wire holder slidably engaged to an inner member of the catheter based stent-graft delivery system, engagement wires, a wire guide fixedly mounted to the inner member of the catheter based stent-graft delivery system distal to the wire holder, and a distal receiver fixedly mounted to the inner member of the catheter based stent-graft delivery system distal from the wire guide, and eyelets integral with a stent-graft and extending from the end thereof, the engagement wires originating from the wire holder, passing through the wire guide, the eyelets and into distal receiver, the wire holder being configured to move proximally, thereby retracting the engagement wires from the distal receiver and eyelets and into the wire guide.

The present invention is directed to a stent-graft securement mechanism, in which both the stent-graft and the delivery device or delivery catheter are modified. Essentially, the stent-graft securement mechanism comprises a holding device which is integral with the delivery catheter and an eyelet configuration integral with the distal end of the stent-graft. Each of these components is designed to mate and work with the other in order to achieve the desired functions; namely, to overcome the drawbacks associated with currently utilized stent-graft delivery systems as briefly described above.

The holding device comprises four basic components; namely, the wire holder, the engagement wires, the wire guide and the distal receiver. These four components are integral with the delivery system and function to release the distal end of the stent-graft via action of the physician. The eyelet configuration is an additional element of the stent-graft. The engagement wires simply run from the wire holder, through the wire guide, through the eyelets and into the distal receiver.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 4 is a perspective view of an expanded stent segment of the endovascular graft in accordance with the present invention.

FIG. 4C is an enlarged plan view of a section of the stent segment of FIG. 4.

FIG. 4D is an enlarged plan view of a section of the stent segment of FIG. 4.

DETAILED DESCRIPTION

Figure 1:
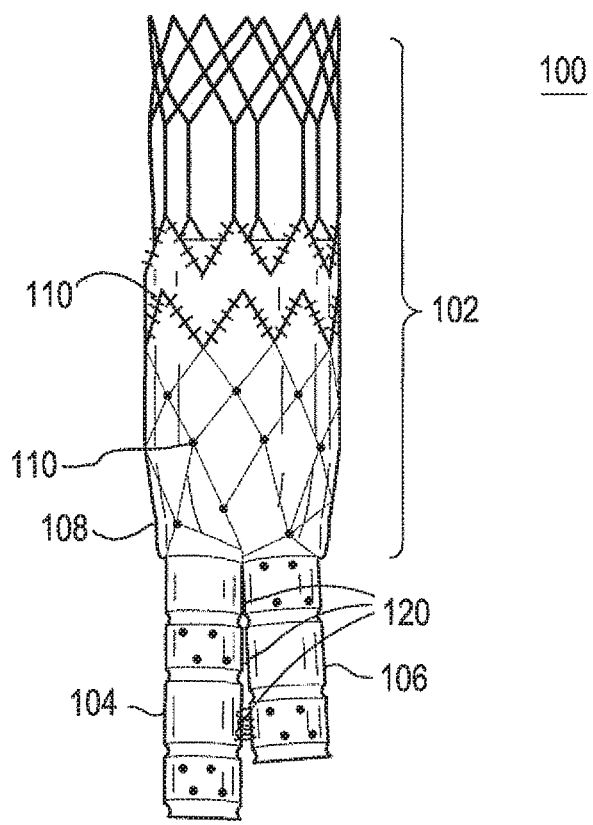
FIG. 1 is a diagrammatic representation of the exemplary anchoring and sealing prosthesis in accordance with the present invention.

Referring to FIG. 1, there is illustrated an exemplary embodiment of an anchoring and sealing component 100 of an aneurysm repair system. The anchoring and sealing component 100 comprises a trunk section 102 and a bifurcated section, including two legs 104, 106. Graft material 108, described in detail below, is affixed to at least a portion of the trunk section 102 and to all of the legs 104, 106. The graft material may be attached via any number of means. In the exemplary embodiment, the graft material 108 is attached to various portions of the underlying structure by sutures 110. As illustrated, the graft material 108 is affixed with a continuous stitch pattern on the end of the trunk section 102 and by single stitches elsewhere. It is important to note that any stitch pattern may be utilized, and other devices, such as staples, may be utilized to connect the graft material 108 to the underlying structure. The sutures 110 may comprise any suitable biocompatible material that is preferably highly durable and wear resistant.

Figure 2:
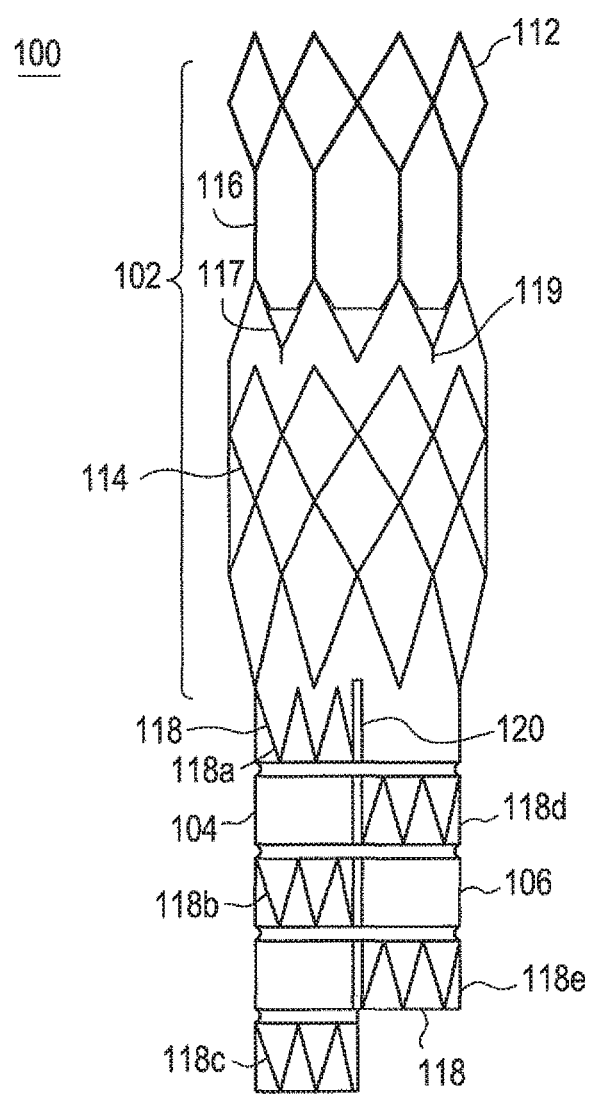
FIG. 2 is a diagrammatic representation of an exemplary anchoring and sealing prosthesis with no graft material and/or stitching in certain locations in accordance with the present invention.

The underlying structure of the trunk section 102, as illustrated in FIG. 2, comprises a substantially tubular stent structure or lattice comprising multiple stent sections. The stent or lattice structure comprises a single row of substantially diamond shaped elements 112 on one end, multiple rows of substantially diamond shaped elements 114 on the other end, a plurality of longitudinal struts 116 and a single, substantially zigzag shaped stent element 117. The plurality of longitudinal struts 116 are connected to the apexes of the substantially diamond shaped elements 114. The single, substantially zigzag shaped stent element 117 comprises a number of barbs 119 protruding therefrom for anchoring the device in the vessel to be repaired. This exemplary embodiment may be utilized for anchoring and sealing in positions wherein there are branches off the main artery. For example, this exemplary embodiment may be utilized for supra-renal anchoring. Accordingly, the graft material 108 is only attached below the longitudinal struts 116 so that blood may flow into the renal arteries from the aorta. Infra-renal designs are also possible.

The underlying structure of the bifurcated section, as illustrated in FIG. 2, comprises a plurality of individual, substantially tubular stent elements 118. Each stent element 118 comprises a substantially zigzag pattern. As illustrated, leg 104 comprises three stent elements 118a, 118b, 118c and leg 106 comprises two stent elements 118d, 118e. As illustrated, in this exemplary embodiment, the stent elements do not line up and the legs are of two different lengths. This exemplary design allows for nesting of the legs 104, 106 such that the profile of the device is reduced.

In order to compensate for the missing stent elements, the legs are connected at the bifurcation as illustrated in FIG. 1. The legs 104, 106 may be connected in any suitable manner. In the exemplary embodiment, the two legs 104, 106 are connected by suturing them together. The sutures 120 connect the graft material 108 on each leg 104, 106 together. The sutures may be non-biodegradable or biodegradable. Biodegradable sutures would dissolve over time thereby allowing the two legs to move independently.

Figure 3:
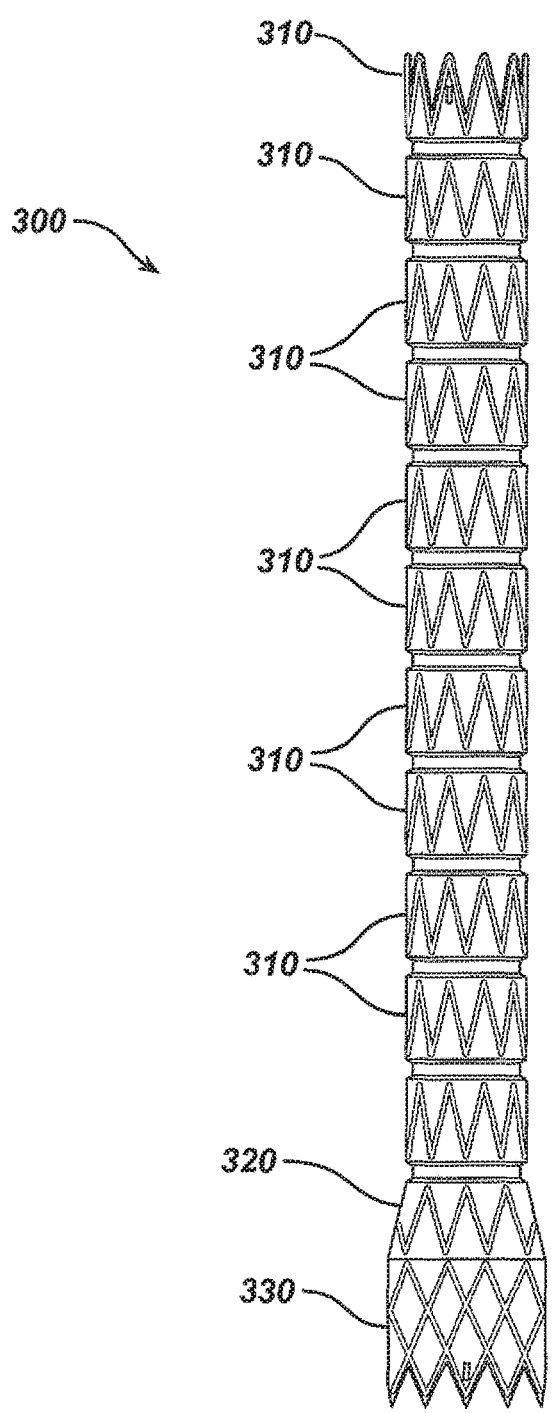
FIG. 3 is an elevational view of an endovascular graft in accordance with the present invention.

Referring now to FIG. 3, there is illustrated an exemplary embodiment of an endovascular graft 300 of an aneurysm repair system. The exemplary endovascular graft 300 comprises one or more first stent segments 310, one second stent segment 320 and a third stent segment 330. In a typical use scenario, the third stent segment 330 would be anchored in healthy tissue below the aneurysm and the uppermost first stent segment 310 would be in fluid communication with the anchoring and sealing component 100. The second stent segment 320 comprises a tapered profile, having a diameter at one end equal to that of the first stent segment 310 and a diameter at the other end equal to that of the third stent segment 330. The length of the endovascular graft 300 may be adjusted by varying the number of first stent segments 310 utilized.

Figure 4A:
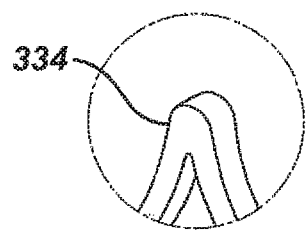
FIG. 4A is a fragmentary perspective view of a portion of the stent segment of FIG. 4.
Figure 4B:
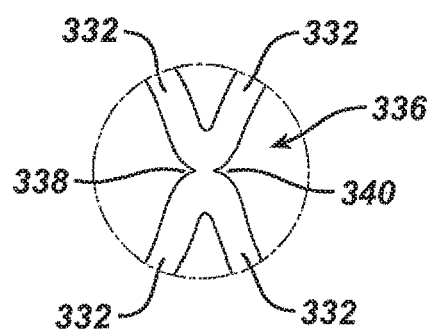
FIG. 4B is a fragmentary perspective view of a portion of the stent segment of FIG. 4.

FIG. 4 is a detailed perspective view of an exemplary embodiment of the third stent segment 330. The third stent segment 330 comprises a plurality of struts 332 connected in a substantially zigzag pattern. As illustrated, the exemplary third stent segment 330 comprises three sets of zigzag-connected struts 332, thereby forming substantially diamond-shaped cells. The non-connected apex 334 of each diamond shaped cell, illustrated in greater detail in FIG. 4A, comprises a smooth, uniform width curved region formed at the intersection of two struts 332 of each diamond-shaped cell. This shape is cut directly into the stent segment 330 during the initial machining steps, typically laser cutting, and is maintained during all subsequent finishing processing. The junctions 336 between the zigzag-connected struts 332, illustrated in greater detail in FIG. 4B occurs at the intersection of four struts 332. Preferably, each junction 336 of four struts 332 comprises two indentations 338 and 340 as illustrated in FIG. 4B.

The regions proximate the non-connected apexes 334 and the junctions 336 are generally the highest stress regions in the third stent segment 330. To minimize the stresses in these regions, these regions are designed to maintain uniform beam widths proximate where the struts 332 interconnect. Beam width refers to the width of a strut junction 336. Indentations 338 and 340 are cut or machined into the junctions 336 to maintain a uniform beam width in this area, which is generally subject to the highest stress. Essentially, by designing the junctions 336 to maintain uniform beam widths, the stress and strain that would normally build up in a concentrated area, proximate the junction 336, is allowed to spread out into the connecting regions, thereby lowering the peak values of the stress and strain in the stent structure.

To further minimize the maximum stresses in the struts 332 of the third stent segment 330, the struts 332 may have a tapering width. For example, in one exemplary embodiment, the struts 332 may be designed to become wider as it approaches a junction 336. FIG. 4C is an enlarged partial view of the third sent segment 330 in its expanded conditions which illustrates the tapering width of the struts 332. In this exemplary embodiment, the strut 332 proximate the junction 336 (width a) is about 0.025 cm and gradually tapers to a dimension of about 0.0178 cm in the mid-region of the strut 332 (width b). By tapering the struts' widths, the stresses in the struts 332 adjacent the junction 336 is spread out away from the junction 336. The tapering of the struts 332 is accomplished during the machining of the tube of material from which the stent 330 is cut. However, by tapering the struts 332 in this manner, there is a tradeoff. The stent segment 330 becomes somewhat less resistant to localized deformations, caused for example, by a protrusion within the vessel lumen. This localized deformation may lead to a local torsional loading on some of the struts 332, and, therefore, since the struts 332 in this exemplary embodiment have a relatively significant portion of their length with a reduced width, their torsional rigidity is reduced.

If maximizing the resistance to localized deformation is preferred, the struts 332 may be maintained at a uniform width, or more preferably have a reverse taper, as illustrated in FIG. 4D, wherein the width at point a is less than the width at point b. In this exemplary embodiment, the reverse taper struts 332 are about 0.025 cm proximate the junction 336 and about 0.028 cm in the central region of the struts. While this reverse taper tends to increase the stresses somewhat proximate the junctions 336, this increase is very small relative to the decrease in stresses gained by having the side indentations 338, 340 illustrated in FIG. 4B, as well as the uniform width connections illustrated in FIG. 4A. In addition, since the reverse taper serves to increase the torsional rigidity of the strut 332, the stent structure resists local deformation and tends to maintain a substantially circular cross-sectional geometry, even if the lumen into which the stent is positioned in non-circular in cross-section.

In a preferred exemplary embodiment, the third stent segment 330 is fabricated from a laser cut tube, of initial dimensions 0.229 cm inside diameter by 0.318 cm outside diameter. The struts 332 are preferably 0.0229 cm wide adjacent the four strut junctions 336 and six mm long, with a reverse taper strut width. Also, to minimize the number of different diameter combination of grafts systems, it is preferred that the third stent segment 330 have an expanded diameter of sixteen mm. Similarly, the proximal portion of the graft material forming the legs is flared, having a diameter of sixteen mm. This single diameter for the third stent segment of the graft system would enable its use in arteries having a non-aneurysmal region of a diameter from between eight and fourteen mm in diameter. It is also contemplated that multiple diameter combinations of third stent segment 330 and graft flare would be desirable.

Figure 5:
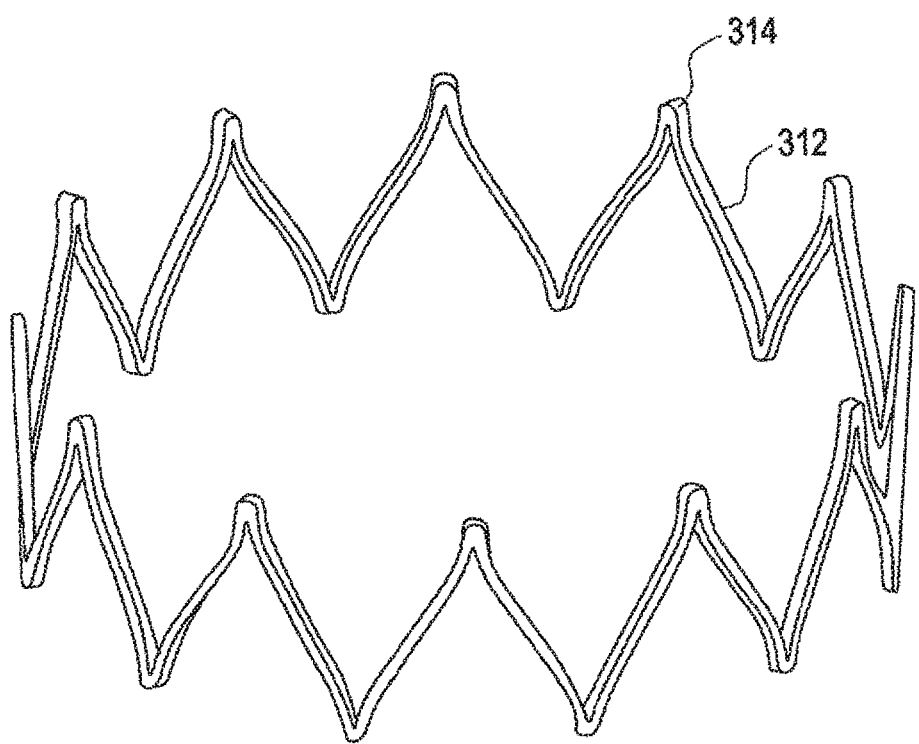
FIG. 5 is a perspective view of another expanded stent segment of the endovascular graft in accordance with the present invention.

Referring back to FIG. 3, the one or more first stent segments 310 are also formed from a shape set laser cut tube, similar to the third stent segment 330 described above. The one or more first stent segments 310 comprise a single circumferential row of zigzag or sinusoidally arranged elements. In the exemplary embodiment illustrated in FIG. 3, and in greater detail in FIG. 5, the first stent segment 310 comprises ten zigzag or sinusoidal undulations. The one or more first stent segments 310 are formed with uniform width connections at the intersections 314 of the struts 312 forming the zigzag or sinusoidal pattern. The one or more first stent segments 310 are preferably cut from tubing having an inside diameter of 0.251 cm and an outside diameter of 0.317 cm. The strut widths are preferably about 0.33 cm wide adjacent strut intersections 314 and the struts 312 are preferably seven mm long and the one or more first stent segments 310 are preferably eleven mm in diameter when expanded.

The second stent segment 320 comprises a tapered profile, having a diameter at one end which is the same as the one or more first stent segments 310, and a diameter at the other end matching the diameter of the third stent segment 330. The second stent segment 320 is identical to the one or more first stent segments 310 except for the taper.

As is explained in detail subsequently, the stent segments 310, 320 and 330 are secured in position by the graft material.

Nitinol is utilized in a wide variety of applications, including medical device applications as described herein. Nitinol or Ni—Ti alloys are widely utilized in the fabrication or construction of medical devices for a number of reasons, including its biomechanical compatibility, its biocompatibility, its fatigue resistance, its kink resistance, its uniform plastic deformation, its magnetic resonance imaging compatibility, its constant and gentle outward pressure, its dynamic interference, its thermal deployment capability, its elastic deployment capability, its hysteresis characteristics and because it is modestly radiopaque.

Nitinol, as described above, exhibits shape memory and/or superelastic characteristics. Shape memory characteristics may be simplistically described as follows. A metallic structure, for example a Nitinol tube that is in an Austenite phase may be cooled to a temperature such that it is in the Martensite phase. Once in the Martensite, the Nitinol tube may be deformed into a particular configuration or shape by the application of stress. As long as the Nitinol tube is maintained in the Martensite phase, the Nitinol tube will remain in its deformed shape. If the Nitinol tube is heated to a temperature sufficient to cause the Nitinol tube to reach the Austenite phase, the Nitinol tube will return to its original or programmed shape. The original shape is programmed to be a particular shape by well known techniques. Superelastic characteristics may be simplistically described as follows. A metallic structure, for example, a Nitinol tube that is in an Austenite phase may be deformed to a particular shape or configuration by the application of mechanical energy. The application of mechanical energy causes a stress induced Martensite phase transformation. In other words, the mechanical energy causes the Nitinol tube to transform from the Austenite phase to the Martensite phase. By utilizing the appropriate measuring instruments, one can determine that the stress from the mechanical energy causes a temperature drop in the Nitinol tube. Once the mechanical energy or stress is released, the Nitinol tube undergoes another mechanical phase transformation back to the Austenite phase and thus its original or programmed shape. As described above, the original shape is programmed by well known techniques. The Martensite and Austenite phases are common phases in many metals.

Medical devices constructed from Nitinol are typically utilized in both the Martensite phase and/or the Austenite phase. The Martensite phase is the low temperature phase. A material in the Martensite phase is typically very soft and malleable. These properties make it easier to shape or configure the Nitinol into complicated or complex structures. The Austenite phase is the high temperature phase. A material in the Austenite phase is generally much stronger than the material in the Martensite phase. Typically, many medical devices are cooled to the Martensite phase for manipulation and loading into delivery systems, as described above with respect to stents and then when the device is deployed at body temperature, they return to the Austenite phase.

The first, second and third stent segments 310, 320, 330 are preferably self-expandable and formed from a shape memory alloy. Such an alloy may be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising about 55.8 percent Ni by weight, commercially available under the trade designation NITINOL. This NiTi alloy undergoes a phase transformation at physiological temperatures. A stent made of this material is deformable when chilled. Thus, at low temperatures, for example, below twenty degrees centigrade, the stent is compressed so that it can be delivered to the desired location. The stent may be kept at low temperatures by circulating chilled saline solutions. The stent expands when the chilled saline is removed and it is exposed to higher temperatures within the patient's body, generally around thirty-seven degrees centigrade.

In preferred embodiments, each stent is fabricated from a single piece of alloy tubing. The tubing is laser cut, shape-set by placing the tubing on a mandrel, and heat-set to its desired expanded shape and size.

In preferred embodiments, the shape setting is performed in stages at five hundred degrees centigrade. That is, the stents are placed on sequentially larger mandrels and briefly heated to five hundred degrees centigrade. To minimize grain growth, the total time of exposure to a temperature of five hundred degrees centigrade is limited to five minutes. The stents are given their final shape set for four minutes at five hundred fifty degrees centigrade, and then aged to a temperature of four hundred seventy degrees centigrade to import the proper martensite to austenite transformation temperature, then blasted, as described in detail subsequently, before electropolishing. This heat treatment process provides for a stent that has a martensite to austenite transformation which occurs over a relatively narrow temperature range; for example, around fifteen degrees centigrade.

To improve the mechanical integrity of the stent, the rough edges left by the laser cutting are removed by combination of mechanical grit blasting and electropolishing. The grit blasting is performed to remove the brittle recast layer left by the laser cutting process. This layer is not readily removable by the electropolishing process, and if left intact, could lead to a brittle fracture of the stent struts. A solution of seventy percent methanol and thirty percent nitric acid at a temperature of minus forty degrees centigrade or less has been shown to work effectively as an electropolishing solution. Electrical parameters of the electropolishing are selected to remove approximately 0.00127 cm of material from the surfaces of the struts. The clean, electropolished surface is the final desired surface for attachment to the graft materials. This surface has been found to import good corrosion resistance, fatigue resistance, and wear resistance.

Figure 6:
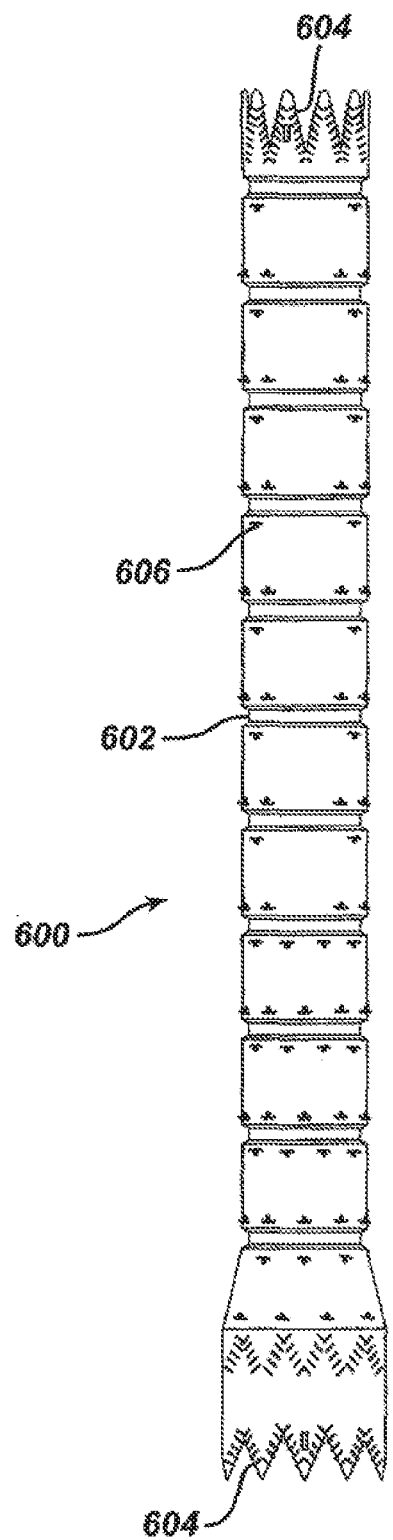
FIG. 6 is an elevational view of an endovascular graft in accordance with the present invention.

The graft material or component 600, as illustrated in FIG. 6, may be made from any number of suitable biocompatible materials, including woven, knitted, sutured, extruded, or cast materials comprising polyester, polytetrafluoroethylene, silicones, urethanes, and ultralight weight polyethylene, such as that commercially available under the trade designation SPECTRA™. The materials may be porous or nonporous. Exemplary materials include a woven polyester fabric made from DACRON™ or other suitable PET-type polymers.

In one exemplary embodiment, the fabric for the graft material is a forty denier (denier is defined in grams of nine thousand meters of a filament or yarn), twenty-seven filament polyester yarn, having about seventy to one-hundred end yarns per cm per face and thirty-two to forty-six pick yarns per cm face. At this weave density, the graft material is relatively impermeable to blood flow through the wall, but is relatively thin, ranging between 0.08 and 0.12 mm in wall thickness.

The graft component 600 is a single lumen tube and preferably has a taper and flared portion woven directly from the loom, as illustrated for the endovascular graft 300 shown in FIG. 3.

Prior to attachment of the graft component 600 to the stents 310, 320, 330, crimps are formed between the stent positions by placing the graft material on a shaped mandrel and thermally forming indentations in the surface. In the exemplary embodiment illustrated in FIGS. 3 and 6, the crimps 602 in the graft 400 are about two mm long and 0.5 mm deep. With these dimensions, the endovascular graft 300 can bend and flex while maintaining an open lumen. Also, prior to attachment of the graft component 600 to the stents 310, 320 330, the graft material is cut in a shape to mate with the end of each end stent.

As stated above, each of the stent segments 310, 320 and 330 is attached to the graft material 600. The graft material 600 may be attached to the stent segments 310, 320, 330 in any number of suitable ways. In one exemplary embodiment, the graft material 600 may be attached to the stent segments 310, 320, 330 by sutures.

The method of suturing stents in place is important for minimizing the relative motion or rubbing between the stent struts and the graft material. Because of the pulsatile motion of the vasculature and therefore the graft system, it is possible for relative motion to occur, particularly in areas where the graft system is in a bend, or if there are residual folds in the graft material, due to being constrained by the aorta or iliac arteries.

Ideally, each strut of each stent segment is secured to the graft material by sutures. In an exemplary embodiment, the suture material is blanket stitched to the stent segments at numerous points to securely fasten the graft material to the stent segments. As stated above, a secure hold is desirable in preventing relative motion in an environment in which the graft system experiences dynamic motion arising from pulsatile blood pressure, in addition to pulsation of the arteries that are in direct mechanical contact with the graft system. The stents nearest the aortic and iliac ends of the graft system (the uppermost first stent segment 310 and the third stent segment 330 respectively) are subject to the pulsatile motion arising from direct internal contact. These struts in particular should be well secured to the graft material. As illustrated in FIG. 6, the stitches 604 on the upper most first stent segment 310 are positioned along the entire zigzag arrangement of struts. The upper and lower apexes of the third stent segment may be stitched utilizing a similar configuration. It is difficult to manipulate the suture thread precisely around the struts that are located some distance away from an open end, accordingly, various other simpler stitches may be utilized on these struts, or no stitches may be utilized in these areas.

As illustrated in FIG. 6, each of the struts in the first stent segment 310 is secured to the graft material 600 which has been cut to match the shape of the stent segment 310. The blanket stitching 604 completely encircles the strut and bites into the graft material 600. Preferably, the stitch 604 encircles the strut at approximately five equally spaced locations. Each of the struts on each end of the third stent segment 330 is attached to the graft material, which has been cut to make the shape of the stent segment 330, in the same manner as the first stent segment 310.

A significant portion of the graft will not rest directly against vascular tissue. This portion of the graft will be within the dilated aneurysm itself. Therefore, this portion of the graft will not experience any significant pulsatile motion. For this reason, it is not necessary to secure the stent segments to the graft material as aggressively as the stent structure described above. Therefore, only point stitches 606 are necessary for securing these stents.

It is important to note that a wide variety of sutures are available. It is equally important to note that there are a number of alternative means for attaching the graft material to the stent, including welding, gluing and chemical bonding.

In accordance with another exemplary embodiment, the present invention is directed to a device for restraining the cranial end of an endoprosthesis, such as an aneurysmal repair device component, after the remaining portion of the endoprosthesis has been partially or fully deployed and expands. Some aneurysmal repair system endoprostheses have a bare metal stent portion that extends past the cranial end of the graft in order to provide some level of supra renal fixation and/or anchoring, see FIG. 1. This stent is in addition to other stents along the length of the prosthesis that are generally used to expand the graft material into position. Barbs or hooks are often employed on the supra renal stent to positively engage the vessel wall as is described in detail herein.

Typically, the endoprosthesis is loaded into a catheter for delivery to the targeted site. During deployment the endoprosthesis is held stationary while the outer catheter sheath is retracted and the endoprosthesis expands into position due to the self expanding properties of the graft material and/or the underlying stent structure. Due to the tortuous nature of the human anatomy, the delivery catheter comprising the endoprosthesis generally lies up against one side of the vessel prior to deployment. It has been observed in testing that when a supra renal stent with barbs is the first portion of the endoprosthesis to expand, the barbs closest to the vessel wall may make premature contact with the wall before the stent has had a chance to fully expand. This creates a situation where the portion of the stent furthest away from the wall during expansion actually accounts for a disproportionate amount of the expansion of the stent in order for the entire stent to meet the internal diameter of the vessel. The sections of the stent that are up against the wall do not fully expand and the stent will not achieve full opposition against the vessel wall. Delaying the opening of the portion of the supra vessel stent that comprises the barbs allows the other portion of the endoprosthesis to move to the centerline of the vessel for expansion and movement of the unexpanded supra renal stent closer to the center of the vessel lumen. Once this has occurred, subsequent deployment of the supra renal stent with the barbs will not result in the potential problems described above because every portion of the supra renal stent has the opportunity to expand equally since the barbs are not close enough to the wall for premature engagement.

In order to accomplish the above, the present invention utilizes a number of exemplary securing methodologies and associated delivery devices for restraining the supra renal stent so that it may be selectively deployed after a portion of the rest of the endoprosthesis has been fully or partially deployed and expands.

In accordance with one exemplary embodiment of a stent-graft securement mechanism, both the stent-graft and the delivery device or delivery catheter are modified. Essentially, the stent-graft securement mechanism comprises a holding device which is integral with the delivery catheter and an eyelet configuration integral with the distal end of the stent-graft. Each of these components is designed to mate and work with the other in order to achieve the desired functions; namely, to overcome the drawbacks associated with currently utilized stent-graft delivery systems as described above.

Figure 7:
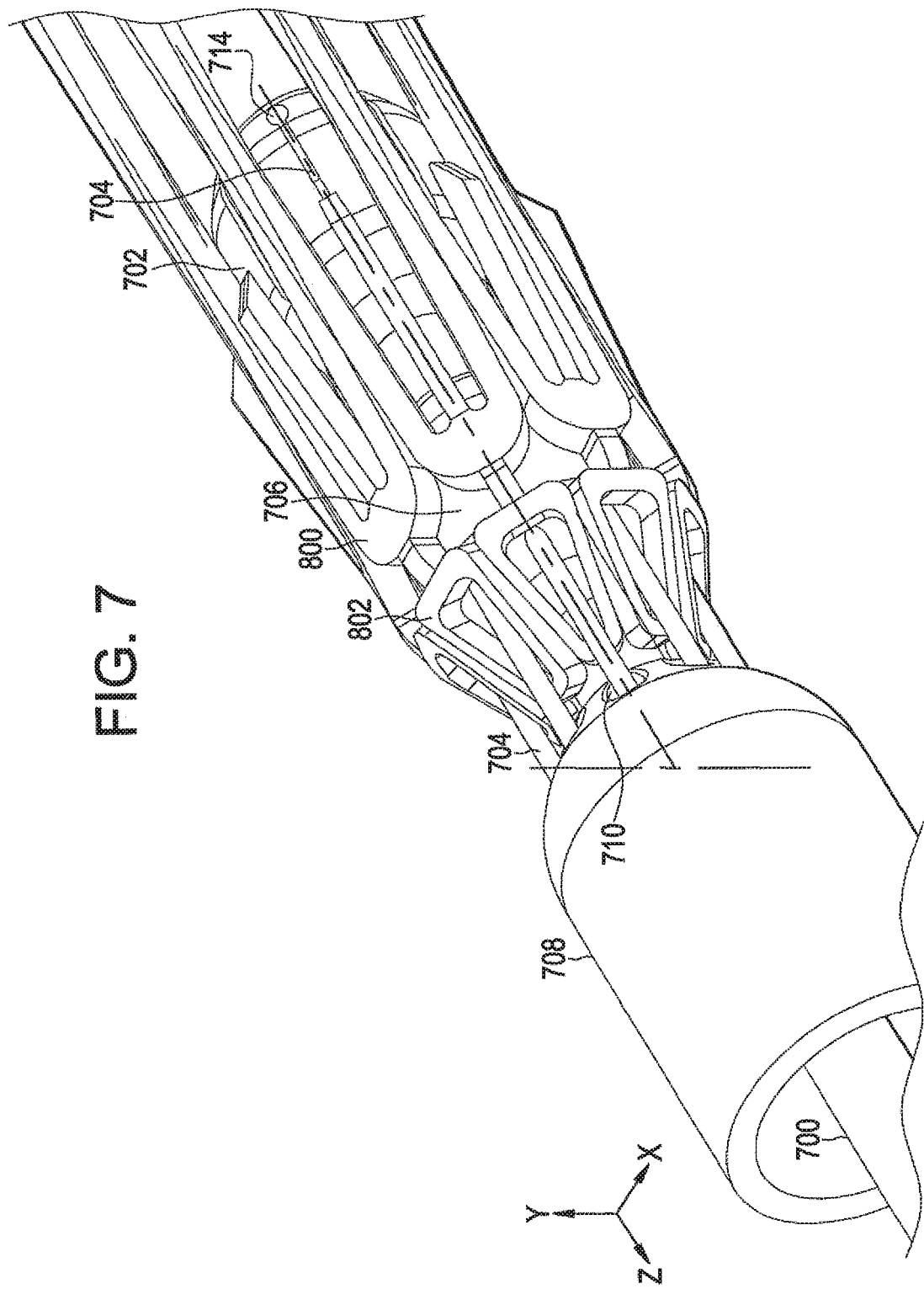
FIG. 7 is a first diagrammatic representation of a portion stent-graft securement device in accordance with the present invention.
Figure 8:
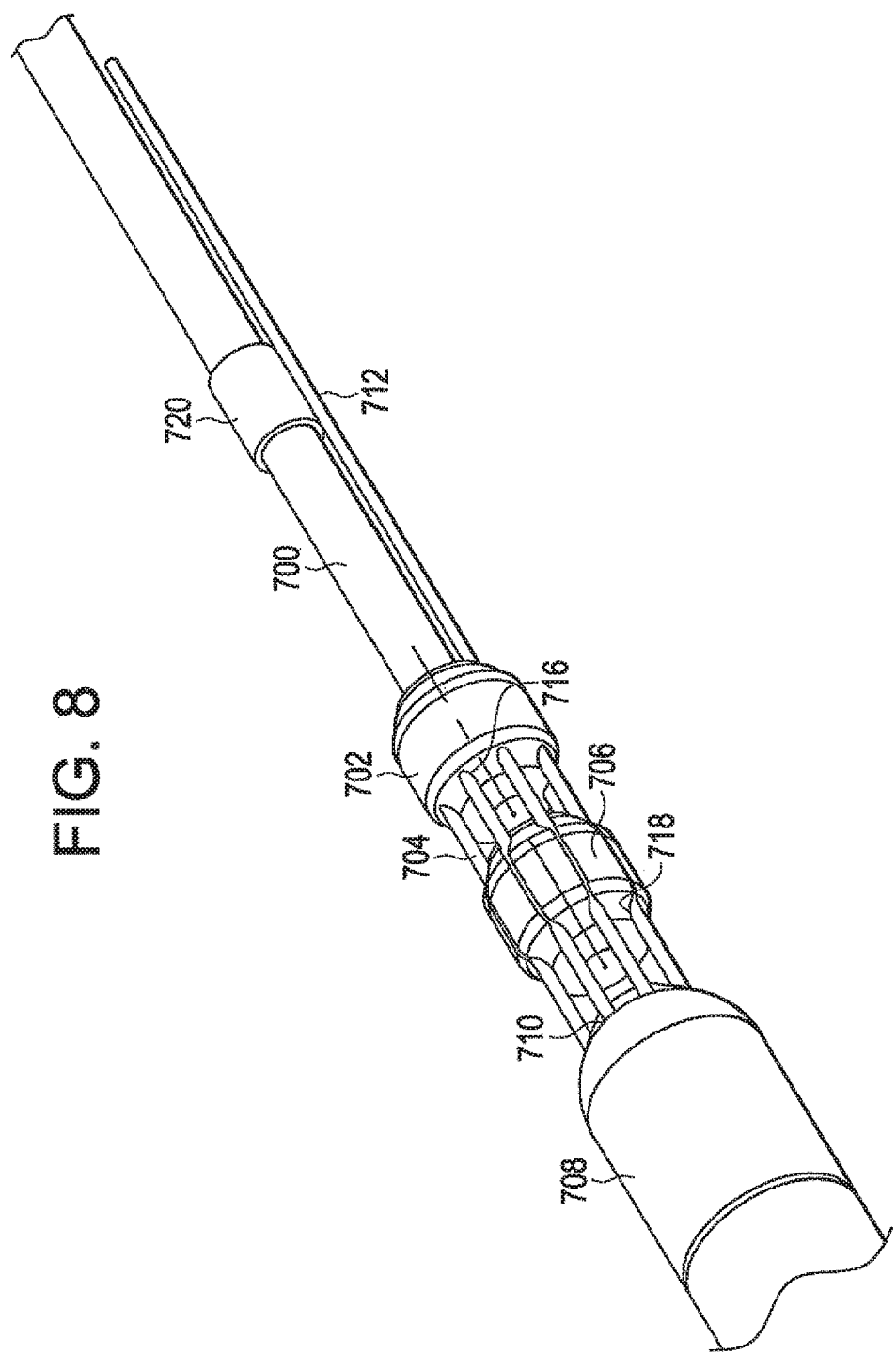
FIG. 8 is a second diagrammatic representation of a portion stent-graft securement device in accordance with the present invention.

Referring now to FIGS. 7 and 8, there is illustrated a section of the distal end of a stent-graft delivery system in accordance with the present invention. FIG. 7 illustrates the delivery system with a stent-graft mounted thereon and FIG. 8 illustrates the delivery system with no stent-graft. The holding device comprises four basic components, the wire holder 702, the engagement wires 704, the wire guide 706 and the distal receiver 708. The wire holder 702 is slidably engaged with the inner member hypotube 700 and functions to hold or secure the engagement wires 704 that pass through the eyelets 802 of the stent-graft 800 as is described in more detail subsequently. The wire holder 702 may comprise any suitable shape or configuration and material. Preferably, the wire holder 702 comprises a substantially tubular configuration and may be formed from stainless steel or polycarbonate. A steel wire holder 702 may be fabricated utilizing machining techniques, while a polycarbonate wire holder 702 may be fabricated utilizing moulding techniques. More specifically, the wire holder 702 comprises beveled or angled ends that are designed to not catch or snag on any other component of the system, including the stent-graft 800 or on the vessel in which the system is deployed. All of the beveled or angled ends described herein have the same degree of angulation. In addition, the wire holder 702 may hold the engagement wires 704 utilizing any suitable means and method. For example, the engagement wires 704 may be held by welding, adhesives, or mechanical means such as tabs 714 on the proximal ends of the engagement wires 704 mating with receptacles in the wire holder 702. As illustrated in FIG. 7, the engagement wires 704 may run along an outer surface of the wire holder 702, or as illustrated in FIG. 8, the engagement wires 704 may run through the wire holder 702 via holes 716. The wire holder 702 also comprises a wire release 712 which may be connected to the wire holder 702 by any suitable means, such as described herein. In operation, the physician pulls on the wire release 712 when he or she is ready to release the distal end of the stent. The wire release runs along the length of the deliver catheter. A more detailed description of a procedure is given subsequently.

The engagement wires 704 originate from the wire holder 702 and extend distally therefrom. The engagement wires 704 pass under the stent-graft 800 and pass through the eyelets 802 until they terminate in the distal receiver 708. The engagement wires 704 may comprise any suitable shape and configuration. Preferably, the engagement wires 704 comprise a substantially cylindrical configuration and may be formed from stainless steel or a polymer. The wires 704 may be of the same length or of varying length. Varying length wires may be particularly useful for utilizing the delivery device for multiple stent-graft deployments. Any number of engagement wires 704 may be utilized. Regardless of the number of engagement 704 utilized, it is preferable that the distal end of the stent-graft 800 be held down until full deployment is required by the medical professional. As stated above, the engagement wires 704 may run through the wire holder 702 (FIG. 8) or along its surface, for example in grooves (FIG. 7).

The wire guide 706 is fixed to the inner member hypotube 700 distal of the wire holder 702. The wire guide 706 may be fixed to the inner member hypotube 700 in any suitable manner, for example, welding, adhesives or via a friction or interference fit. The wire guide 706 slidably engages the engagement wires 704 in order to retain the axial position of the eyelets 802 when the wire holder 702 is withdrawn proximally. In addition, the wire guide 706 may be utilized to capture and secure the distal or free ends of the engagement wires 704. The wire guide 706 may comprise any suitable configuration and be formed from any suitable material. In a preferred exemplary embodiment, the wire guide 706 comprises a substantially tubular configuration and is formed from stainless steel or polycarbonate. More specifically, the wire guide comprises beveled or angled ends so as not to catch on any other component. The wire guide 706 comprises a number of openings corresponding to the number of engagement wires 704 utilized. The openings may comprise grooves or through holes. In the preferred embodiment, through holes 718 are utilized as illustrated in detail in FIG. 8. Although it appears as a groove in FIG. 8, the through holes 718 are created utilizing an electro-machining technique that first creates a slit opening in the work piece.

It is important to eliminate any potential proximal movement of the stent-graft 800 while the securement mechanism is being withdrawn. In addition, it is important to maintain a reduced profile delivery device. Accordingly, the wire guide 706 is designed to solve the movement problem and the eyelet 802 design, as described in detail below, is designed to solve the profile problem. The wire guide 706 is fixed in position, but allows the engagement wires 704 to slide smoothly through it in an axial direction. The wire guide 706 also provides the radial retention force on the engagement wires 704 to prevent the eyelets 802 from opening outwards until the engagement wires 704 are fully withdrawn from the wire guide 706. The geometry of the wire guide 706, bevel or taper, of the wire guide 706 prevents proximal movement of the eyelets 802 due to frictional or bending forces while the engagement wires 704 are being withdrawn, thereby improving deployment accuracy. In addition, the wire guide 706 serves or functions as a housing for the ends of the retracted engagement wires 704, thereby minimizing any potential problems that may be caused by the ends of the engagement wires 704 interacting with the vessel or stent-graft 800.

The distal receiver 708 is fixed to the inner member hypotube 700. The distal receiver 708 comprises a number of openings 710 corresponding to the number of engagement wires 704. Prior to stent release, the distal ends of the engagement wires 704 extend into the openings in the distal receiver 708 where they remain secured. The openings 710 are sized for ease of insertion and ease of removal of the engagement wires 704 while still providing adequate securement of the engagement wires. The distal receiver 708 comprises a diameter larger than the diameter of the inner member hypo tube 700, thereby creating an annular space for the engagement wires 704. The distal receiver 708 may comprise any suitable configuration and be formed from any suitable material. In a preferred exemplary embodiment, the distal receiver 708 comprises a substantially tubular configuration and is formed from stainless steel or a polymer. More specifically, the distal receiver 708 comprises a beveled or angled end on the end with the openings 10. The distal receiver 708 may be fixed to the inner member hypotube 700 by any suitable means. For example, the distal receiver 708 may be fixed to the inner member hypotube through any suitable means, for example, welding, adhesives or via a friction or interference fit.

Figure 9:
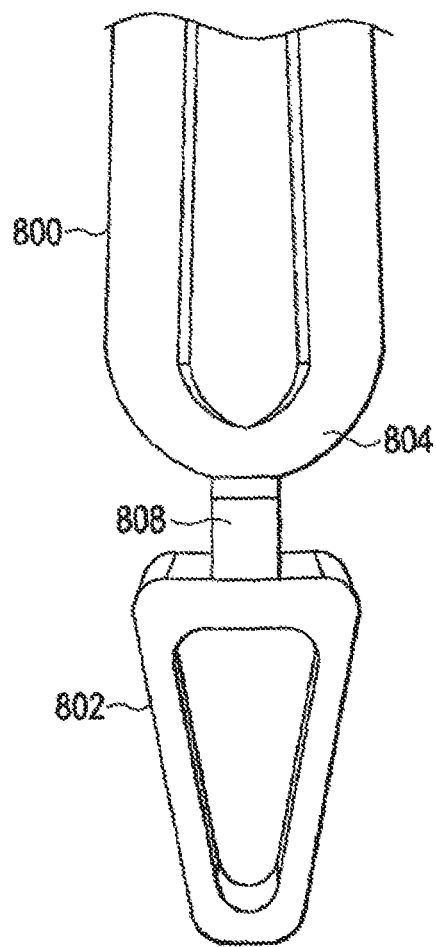
FIG. 9 is a third diagrammatic representation of a portion stent-graft securement device in accordance with the present invention.
Figure 10:
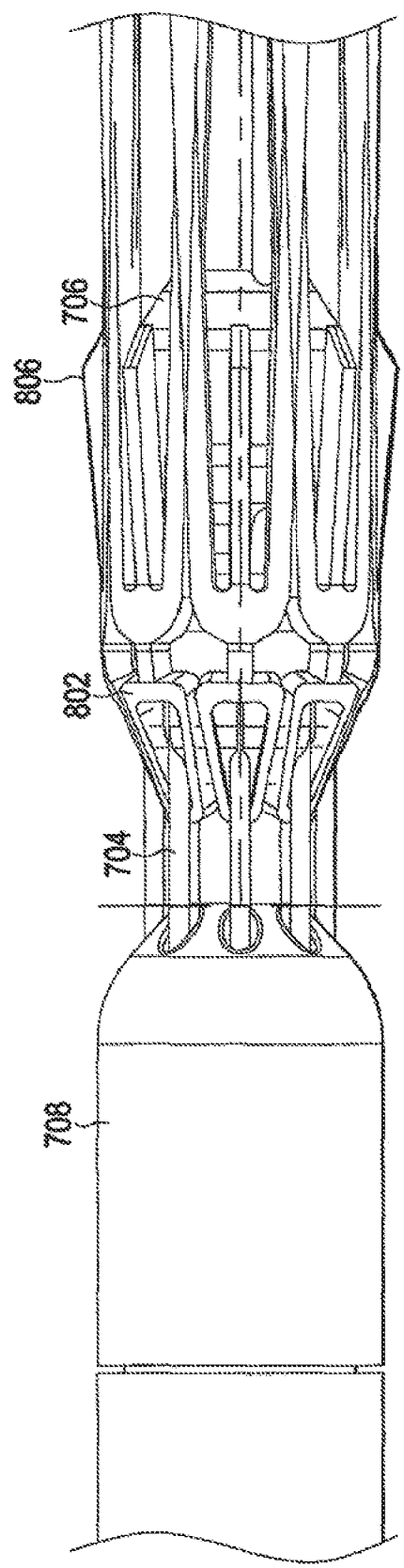
FIG. 10 is a fourth diagrammatic representation of a portion stent-graft securement device in accordance with the present invention.
Figure 11:
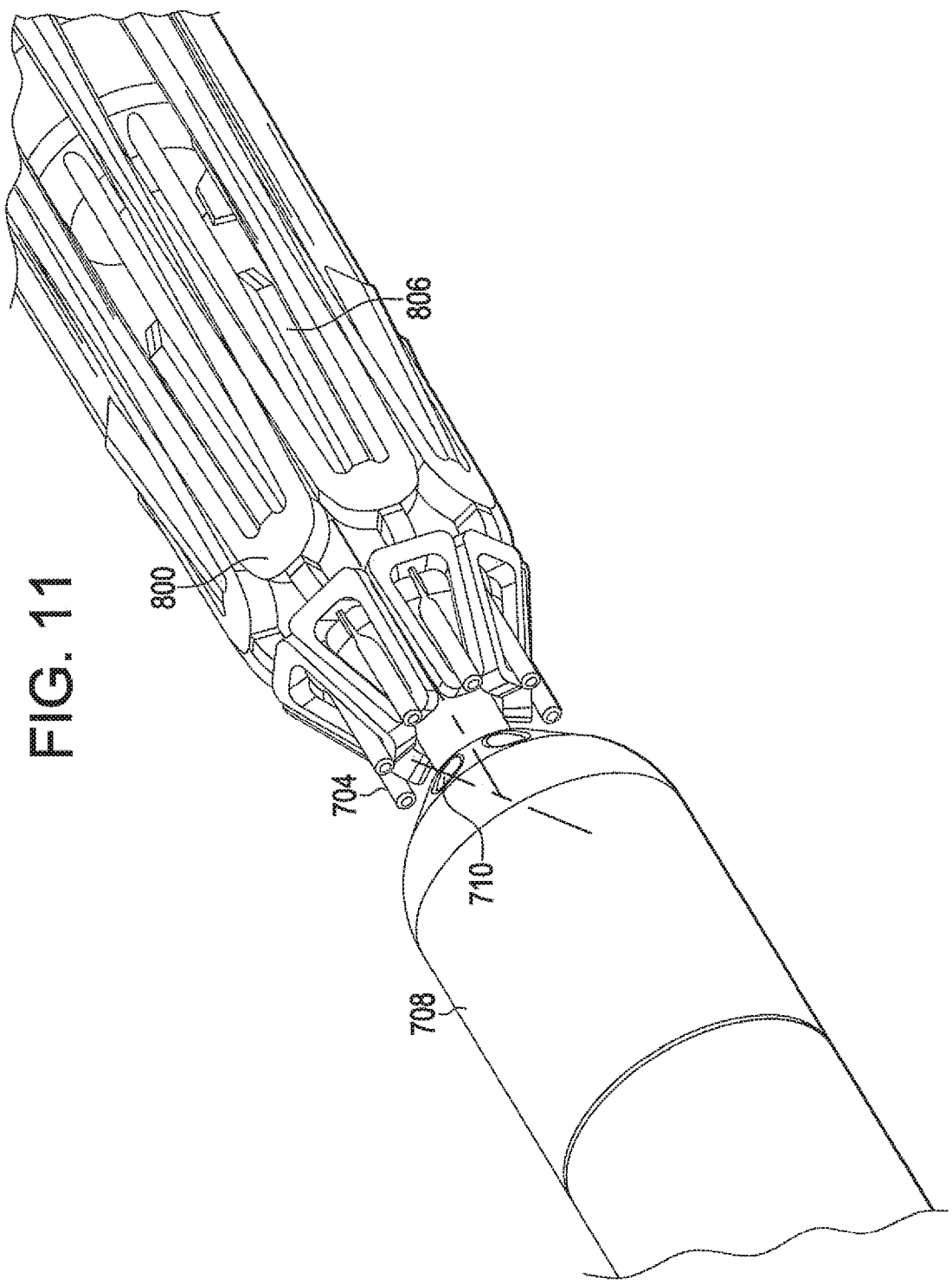
FIG. 11 is a fifth diagrammatic representation of a portion stent-graft securement device in accordance with the present invention.

Referring now to FIGS. 9 through 11, there is illustrated a detailed illustration of a single eyelet 802 of the stent-graft 800 as well as other details of the stent-graft securement mechanism. The eyelets 802 extend from the apexes 804 of the stent-graft 800 and angle inwardly as described above. Opposite from the eyelets 802 are the engagement barbs 806 that secure the expanded stent-graft 800 to the vessel wall. The eyelet 802 may be an additional element attached to the stent-graft 800, or more preferably the eyelet 802 is integral with the stent-graft 800. In other words, the eyelet 802 is simply a feature of the stent-graft 800 cut from the tube that the stent-graft 800 is cut from as described above. The eyelets 802 extend from the apexes 804 via protrusions 808. As above with respect to the eyelets 802, the protrusions 808 are cut from the same tube. Each eyelet 802 is configured or designed to have a narrow geometry which enables the stent-graft to be crimped while allowing sufficient room for the engagement wires to pass under the stent-graft 800 and through the eyelets 802. The unique configuration of the eyelet 802 that enables this is the tapered and angled configuration. As illustrated in the Figures, the eyelet 802 is angled axially inward toward the center of the stent-graft 800. The angle of the eyelet 802 relative to the stent 800 is substantially equal to that of beveled or angled ends of the wire guide 706. Each eyelet 802 also comprises a tapered structure forming a substantially triangular configuration. These two features allow the engagement wires 704 to easily pass through the eyelets 802 as well as provide a reduced profile for delivery. The tightly nested surfaces also minimize axial movement of the stent-graft 800 when the engagement wires 704 are engaged.

It is important to note that the eyelets 802 may formed from sutures and attached to the stent-graft 800. Alternatively, sutures may be utilized to augment the eyelets 802.

Recalling that it is desired to maintain a reduced profile and reduce unnecessary movement, the eyelets 802 have a substantially triangular or arrowhead configuration that allows the stent-graft 800 to be compressed without strut overlap. In addition, mating the angle of the eyelet 802 to the wire guide 706 allows for a secure nesting of the stent-graft to the delivery system.

Figure 12:
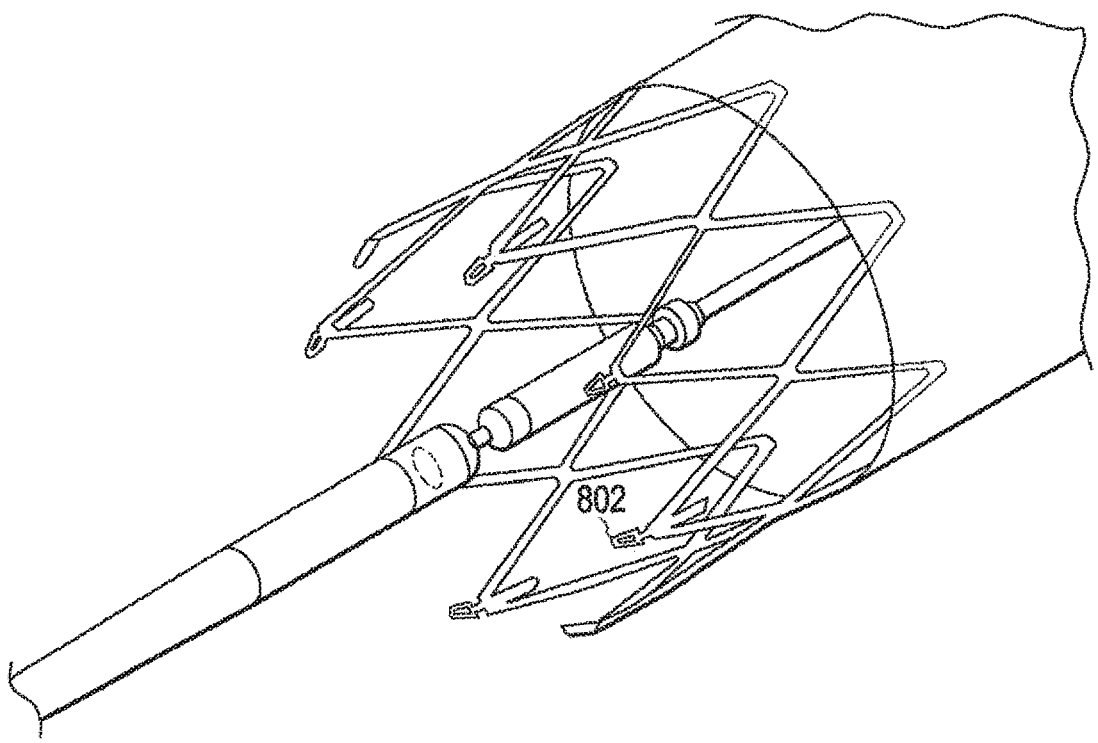
FIG. 12 is a sixth diagrammatic representation of a portion stent-graft securement device in accordance with the present invention.

In operation, the medical professional positions the stent-graft 800 in the desired location and retracts the outer sheath thereby exposing the stent-graft and allowing a portion of it to expand. Once this operation is complete, the medical professional may retract the wire holder 702 via the wire release 712. The wire release 712 is simply a wire connected to the wire holder 702 and which runs along the length of the delivery system to a point where the physician has easy access, such as proximate the handle of the delivery system. This operation allows the distal end of the stent-graft 800 to expand as illustrated in FIG. 12.

FIG. 11 illustrates the engagement wires 704 retracted from the distal receiver 708. To complete the procedure, the physician simply continues to pull the wire release 712 proximally, thereby further retracting the wire holder 702 and freeing the eyelets 802 from the engagement wires. Preferably, the physician will retract the engagement wires 704 into the wire guide 706 so that no free ends of the engagement wires are exposed. The delivery device typically comprises a proximal stop 720 (FIG. 8). Accordingly, the proximal stop 720 may be utilized to ensure that the free ends of the wires 704 are retracted fully into the wire guide 706 by acting as a stop for the wire holder 702.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An endoprothesis delivery system comprising:
   an elongated shaft having a length, a distal section, and an outer diameter;
   a handle operatively connected to the elongated shaft for positioning the endoprosthesis delivery system;
   a wire holder having a tubular configuration and a distal end and proximal end and an axial length, the wire holder located coaxially about the distal section of the elongated shaft and axially translatable with respect to the elongated shaft;
   a plurality of wires extending distally from the wire holder, having proximal ends secured in the wire holder and terminating in distal free ends;
   a wire guide having an axial length, a proximal end and a distal end beveled at an angle, the wire guide fixedly attached to and coaxially about the elongated shaft distal to the wire holder, the wire guide configured to slidably engage the plurality of wires extending from the wire holder through a plurality of spaces along the axial length of the wire guide, each one of the plurality of spaces aligned with one of the plurality of wires extending from the wire holder;
   a distal receiver fixedly attached to and coaxially about the elongated shaft distal to the wire holder and defining a plurality of spaces, each one of the plurality of spaces aligned with one of the plurality of wires extending from the wire holder such that each one of the plurality of wires extending from the wire holder, when in a secured position, terminates in one of the plurality of spaces within the distal receiver; and
   a single wire fixedly attached to the wire holder and extending proximally from the wire holder to a point proximate the handle of the delivery system such that when the single wire is pulled proximally, the wire holder and the plurality of wires move proximally.

2. The endoprothesis delivery system of claim 1, wherein each one of the plurality of spaces through which one of the plurality of wires extends is shaped such that the wire guide provides a radial retention force on the plurality of wires when the wires experience a radially outward force.

3. The endoprothesis delivery system of claim 2, wherein the proximal end of the wire guide is beveled.

4. The endoprothesis delivery system of claim 1 further comprising a sheath having a length, a proximal end, a distal end, and an inner diameter, the sheath disposed about the elongated shaft.

5. The endoprothesis delivery system of claim 1 further comprising a proximal stop fixedly attached to the distal section of the elongated shaft proximal to the wire holder, the proximal stop extending radially from the outer diameter of the elongated shaft to mechanically interfere with the wire holder when the wire holder moves proximally against it.

6. The endoprothesis delivery system of claim 1, wherein the distal end of the wire holder is beveled.

7. The endoprothesis delivery system of claim 1, wherein the proximal end of the wire holder is beveled.

8. The endoprothesis delivery system of claim 1, wherein the elongated shaft is a hypotube.

9. The endoprothesis delivery system of claim 1, wherein a first wire of the plurality of wires extending distally from the wire holder terminates a first length distal to the wire holder, and a second wire of the plurality of wires extending distally from the wire holder terminates a second length distal to the wire holder, and the first and second length differ.

10. The endoprothesis delivery system of claim 1, wherein a first wire of the plurality of wires extending distally from the wire holder terminates a first length distal to the wire holder, and a second wire of the plurality of wires extending distally from the wire holder terminates a second length distal to the wire holder, and the first and second length are the same.

\* \* \* \* \*